(12) United States Patent
Bloch et al.

(10) Patent No.: US 10,602,837 B2
(45) Date of Patent: Mar. 31, 2020

(54) ORAL CARE IMPLEMENT WITH AUDIO CHANNEL

(71) Applicant: COLGATE-PALMOLIVE COMPANY, New York, NY (US)

(72) Inventors: Brian Bloch, Hillsborough, NJ (US); Lars Ralf Rainer Lieberwirth, Glashuetten (DE)

(73) Assignee: Colgate-Palmolive Company, New York, NY (US)

( * ) Notice: Subject to any disclaimer, the term of this patent is extended or adjusted under 35 U.S.C. 154(b) by 246 days.

(21) Appl. No.: 14/920,818

(22) Filed: Oct. 22, 2015

(65) Prior Publication Data

US 2017/0112272 A1     Apr. 27, 2017

(51) Int. Cl.
| | |
|---|---|
| *A46B 15/00* | (2006.01) |
| *A46B 5/00* | (2006.01) |
| *A46B 9/04* | (2006.01) |
| *A61C 17/22* | (2006.01) |
| *A61C 17/34* | (2006.01) |

(52) U.S. Cl.
CPC .......... *A46B 15/004* (2013.01); *A46B 5/0095* (2013.01); *A46B 9/04* (2013.01); *A46B 15/0008* (2013.01); *A46B 15/0044* (2013.01); *A61C 17/221* (2013.01); *A61C 17/3409* (2013.01); *A46B 2200/1066* (2013.01)

(58) Field of Classification Search
CPC ..... A46B 9/04; A46B 15/008; A46B 15/0044; A46B 15/00; A61C 17/221; A61C 17/3409; G09B 23/28
USPC ........ 15/105, 167.1; 434/263; 446/265, 297, 446/397, 408
See application file for complete search history.

(56) References Cited

U.S. PATENT DOCUMENTS

| | | |
|---|---|---|
| 5,331,707 A | 7/1994 | Irizarry |
| 6,233,773 B1 | 5/2001 | Karge et al. |
| (Continued) | | |

FOREIGN PATENT DOCUMENTS

| | | |
|---|---|---|
| CN | 201061566 Y | 5/2008 |
| DE | 20 2008 01076 | 1/2009 |
| JP | 2013066839 A * | 4/2013 |

OTHER PUBLICATIONS

The International Search Report and the Written Opinion of the International Searching Authority for International Application PCT/US2016/057626 dated Jan. 27, 2017.

*Primary Examiner* — Monica S Carter
*Assistant Examiner* — Katina N. Henson

(57) ABSTRACT

In some embodiments, an oral care implement includes an elongate body extending from a proximal end to a distal end, a head disposed at the distal end of the elongate body, a plurality of bristles disposed at the head, a speaker, a sound chamber, and a water impermeable membrane. The speaker is disposed in the elongate body to emit sound corresponding to audio received from an audio source. Speakers disposed in a distance spaced from the proximal end of the elongate body and is configured to emit sound toward the proximal end of the elongate body. The sound chamber includes an elongate internal space extending from the first opening proximate the speaker the second proximate the proximal end of the elongate body. Sound emitted from the speaker passes through the sound chamber. The water impermeable membrane occludes the sound chamber between the speaker and the proximal end.

24 Claims, 2 Drawing Sheets

(56) References Cited

U.S. PATENT DOCUMENTS

| | | |
|---|---|---|
| 7,774,888 B2 | 8/2010 | Chen |
| 2003/0166373 A1* | 9/2003 | Whitney ............... A61C 17/22 446/71 |
| 2005/0172433 A1 | 8/2005 | Oliver et al. |
| 2007/0074359 A1 | 4/2007 | O'Llynn |
| 2007/0190509 A1* | 8/2007 | Kim ................... A46B 15/0002 434/263 |
| 2008/0307593 A1 | 12/2008 | Lee |
| 2008/0307594 A1* | 12/2008 | Gatzemeyer ........... A46B 5/021 15/105 |
| 2009/0052721 A1 | 2/2009 | Dabrowski |
| 2011/0067189 A1 | 3/2011 | Major |

* cited by examiner

ORAL CARE IMPLEMENT WITH AUDIO CHANNEL

BACKGROUND

Powered oral care implements, such as powered toothbrushes, are conventionally known. Such conventional implements generally include a power source disposed in a cavity in the toothbrush. The power source may be used to power an actuator or other electronic elements in the toothbrush. In some instances, the power source may be used to power a speaker or other audio transmission device, e.g., to play music or other audio while the user brushes her teeth. Most electronics, including speakers, benefit from being kept dry. However, toothbrushes are rarely used in the absence of water or other moisture. Moreover, conventional speakers sufficiently sized for inclusion in a toothbrush may have relatively poor sound quality.

Accordingly, there is a need in the art for improved oral care devices having audio capability. This disclosure is directed at providing such improved devices and/or overcoming one or more problems set forth above and/or other problems of the prior art.

BRIEF SUMMARY

This application describes improved oral care implements. In aspects of this disclosure, an oral care device herein may be embodied as a toothbrush, which includes an elongate body extending from a proximal end to a distal end, a head disposed at the distal end of the elongate body, a plurality of bristles disposed at the head. The oral care implement may also include a speaker and a sound chamber. The speaker may be disposed in the elongate body at a distance spaced from the proximal end. The speaker may also be configured to emit sound toward the proximal end of the elongate body. The sound chamber includes an elongate internal space extending from a first opening proximate the speaker and a second opening proximate the proximal end of the elongate body. Sound emitted from the speaker passes through the sound chamber.

In one or more additional aspects, a water impermeable membrane occludes the sound chamber between the speaker and the proximal end.

In one or more additional aspects, in an oral care implement as described in the preceding paragraph, one or more lateral openings may extend from an external surface of the elongate body to an internal surface of the sound chamber.

In one or more additional aspects, in an oral care implement as described in the preceding paragraph, the one or more lateral openings may be adjacent the proximal end of the elongate body.

In one or more additional aspects, in an oral care implement as described in any of the preceding paragraphs, an end cap may be disposed in the proximal end of the elongate body.

In one or more additional aspects, in an oral care implement as described in any of the preceding paragraphs, a power source may be disposed in the elongate body.

In one or more additional aspects, in an oral care implement as described in any of the preceding paragraphs, the sound chamber may comprise a first portion and a second portion, and the toothbrush may further include a removable cartridge disposed in the elongate body, wherein a first portion of the sound chamber may be disposed in the elongate body and the removable cartridge may include the second portion of the sound chamber.

In one or more additional aspects, in an oral care implement as described in the preceding paragraph, a seal may seal the removable cartridge relative to the elongate body.

In one or more additional aspects, in an oral care implement as described in the preceding two paragraphs, a seal may seal the first portion of the sound chamber relative to the second portion of the sound chamber.

In one or more additional aspects, in an oral care implement as described in any of the preceding three paragraphs, the removable cartridge may comprise a battery.

In one or more additional aspects, in an oral care implement as described in any of the preceding four paragraphs, one or more lateral openings may extend from an external surface of the cartridge to an internal surface of the second portion of the sound chamber.

In one or more additional aspects, in an oral care implement as described in any of the preceding paragraphs, the water-impermeable membrane may comprise polytetrafluoroethylene.

In another aspect of this disclosure, an oral care implement includes a handle defining a receptacle accessible via a proximal end of the handle; a speaker disposed in the handle at a distance from the proximal end and positioned to transmit sound toward the proximal end; a first sound chamber extending from a position proximate the speaker to the receptacle; and a cartridge disposed in the receptacle, the cartridge comprising a second sound chamber aligned with the first sound chamber.

In one or more additional aspects, in an oral care implement as described in the preceding paragraph, a seal may be disposed between the cartridge and the receptacle.

In one or more additional aspects, in an oral care implement as described in the preceding paragraph, the seal may be disposed between the first sound chamber and the second sound chamber.

In one or more additional aspects, in an oral care implement as described in any of the preceding three paragraphs, a water impermeable membrane may extend laterally across the first sound chamber or the second sound chamber.

In one or more additional aspects, in an oral care implement as described in any of the preceding four paragraphs, one or more lateral openings may extend from an exterior surface of the cartridge to the second sound chamber.

In one or more additional aspects, in an oral care implement as described in the preceding paragraph, the one or more lateral openings may be adjacent the proximal end of the handle.

In one or more additional aspects, in an oral care implement as described in either of the preceding two paragraphs, the one or more lateral openings may be disposed outside the receptacle.

In one or more additional aspects, in an oral care implement as described in any of the preceding three paragraphs, the one or more lateral openings may be spaced from the proximal end of the handle by a distance along an axial dimension.

In one or more additional aspects, in an oral care implement as described in any of the preceding eight paragraphs, the cartridge may contain a power source.

In one or more additional aspects, in an oral care implement as described in the preceding paragraph, the power source may comprise a battery.

In one or more additional aspects, in a toothbrush as described in any of the preceding ten paragraphs, the cartridge may be removable.

Further areas of applicability of the present disclosure will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

The following description of the preferred embodiments is merely exemplary in nature and is in no way intended to limit the disclosure, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

This disclosure relates generally to oral care implements, and more particularly to powered oral care implements embodied as toothbrushes or other elongate tooth cleaning members. Although certain embodiments and benefits will be described, other implementations, modifications, and/or benefits will be appreciated those having ordinary skill in the art, with the benefit of this disclosure.

Figures 1A, 1B:
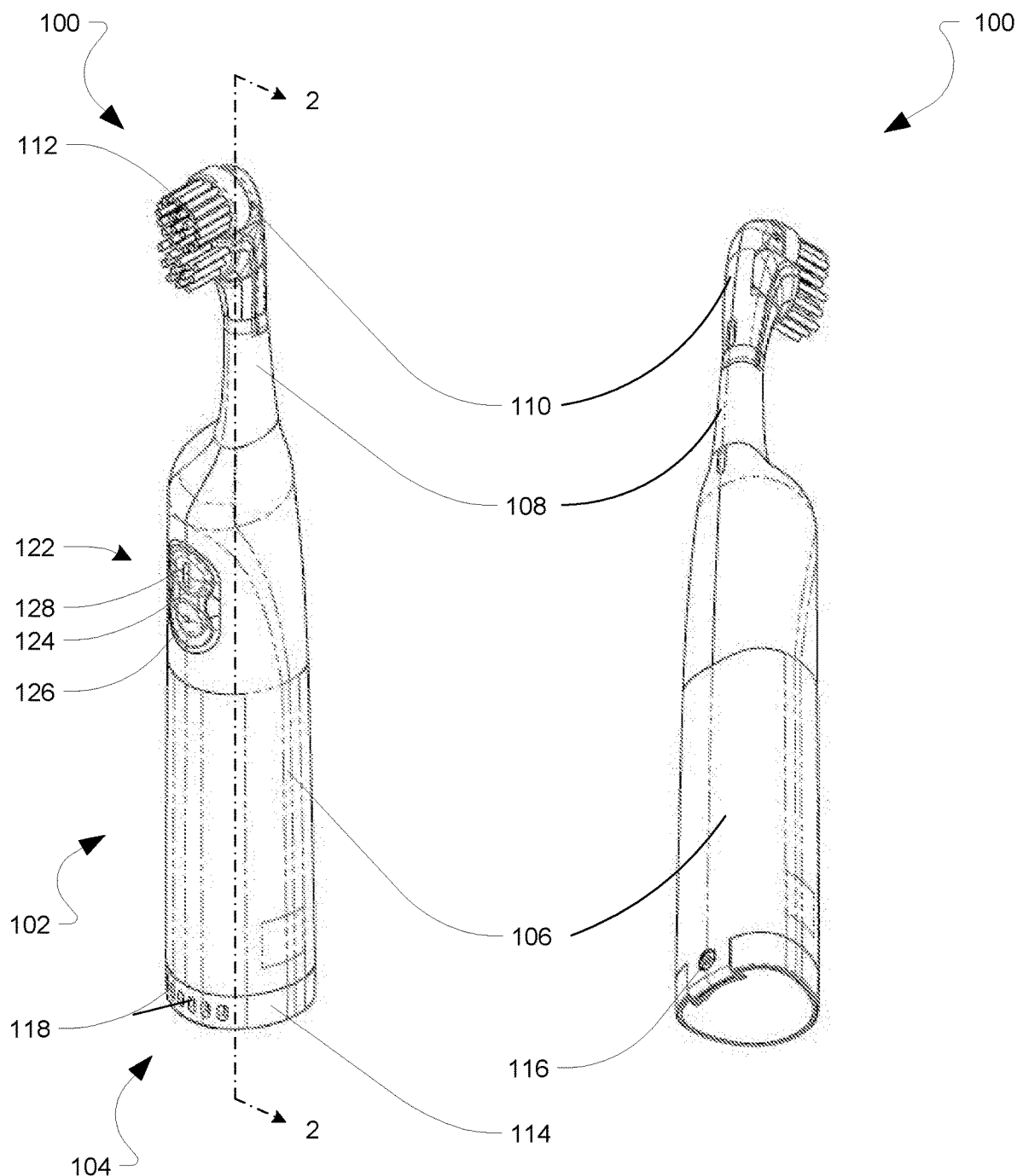
FIG. 1A is a top, front perspective view of an oral care device according to an example implementation of this disclosure.
FIG. 1B is a bottom, rear perspective view of the oral care device depicted in FIG. 1A.

FIGS. 1A and 1B illustrate an oral care device according to implementations of this disclosure. More specifically, those figures are perspective views of an electric-powered toothbrush 100. The toothbrush 100 includes an elongate body 102 extending from a proximal end 104 to a distal end. The body 102 includes a handle 106 and a neck 108. A head 110 is disposed at the distal end of the elongate body 102, at the neck 108. The head 110 supports a plurality of tooth cleaning elements 112. The tooth cleaning elements 112 may be bristles, rubber or polymeric protrusions, or the like. As used herein, the term "tooth cleaning elements" is used in a broad generic sense to refer to any structure that can be used to clean, polish, scrape, whiten, or otherwise interact with the teeth and/or soft oral tissue (e.g., the tongue, the cheek, the gums, etc.) through relative surface contact. Examples of tooth cleaning elements that may be used include, but are not limited to, bristle tufts, filament bristles, fiber bristles, nylon bristles, spiral bristles, rubber bristles, elastomeric protrusions, flexible polymer protrusions, and combinations thereof. Suitable elastomeric materials may include biocompatible resilient materials suitable for use in an oral hygiene apparatus. The tooth cleaning elements 112 may be attached to the head 110 using any suitable method. For example, and without limitation, in-mold tufting or anchor-free tufting may be used to mount the cleaning elements. This disclosure is not limited by the types of tooth cleaning elements 112 or any method of anchoring such tooth cleaning elements 112 to the head 110.

In some embodiments, the head 110 may be detachably mounted to the elongate body 102, for example, to form a replaceable unit or refill such that the user may replace the head after the tooth cleaning elements 112 have been worn. Removal of the head 110 from the elongate body 102 may also allow for the use of different types of tooth cleaning elements 112 with the body 102 or for use of the same body 102 by multiple people. As will be described in more detail below with reference to FIG. 2, in some embodiments the head 110 may include movable features which may allow for relative movement of the tooth cleaning elements 112. For example, some or all of the tooth cleaning elements 112 may move relative to portions of the head 110.

The toothbrush 100 also includes a base 114 at the proximal end 104. In the embodiment depicted in FIGS. 1A and 1B, the base 114 may be removable from the body 102. For example, the base 114 may comprise a cartridge that is selectively removable from a cavity formed as a receptacle in the proximal end of the handle 106. In some embodiments, the base 114 may be removable to access batteries, e.g., for recharging or replacing. As best seen in FIG. 1B, a fastener 116, such as a screw, retains the base 114 in the handle 106. Additional or alternative features also may be provided to promote retention and removal of the base 114 in and from the base 114. Several such features are conventional in the art.

One or more lateral openings 118 also are provided in the base 114. As will be described in more detail below, the openings 118 may be audio openings communicating with an audio chamber that may direct and/or amplify sound emitted from a speaker (not shown in FIGS. 1A and 1B) disposed in the toothbrush 100. Additional openings may also be provided. For instance, generally axially-aligned openings my extend through the base 114 to communicate with the audio chamber, as will be described in more detail, below.

The toothbrush 100 also is illustrated as including a user interface 122. A user interacts with the user interface 122 to control the toothbrush. The user interface 122 may include switches, buttons, actuators, or other interface mechanisms through which the user may control functions of the toothbrush 100. For instance, the user interface 122 is illustrated as including a first button 124 and a second button 126. In some implementations, the first button 124 or the second button 126 may be used to power the toothbrush on and off, e.g., by providing power to a motor to drive the tooth cleaning elements 112. One of the buttons 124, 126 may also be used to power on and off audio functionality associated with the device. Other uses for the buttons 124, 126, as well as other or additional buttons, switches, actuators, and the like also will be understood by those having ordinary skill in the art, with the benefit of this disclosure. For example, but without limitation, one or more of the buttons 124, 126 may be used to cycle through or otherwise select a brushing mode for the toothbrush 100. The toothbrush 100 may be preprogrammed with a number of oscillation patterns or other movement patterns, each of which may promote oral care. In still other embodiments, the buttons 124, 126 may be used to adjust the volume of an audio output or otherwise control audio capabilities. The user interface 122 also is illustrated as including a visual indicator 128. The visual indicator 128 may be an LED or other light emitting device that may convey information. For example, the visual indicator may inform the user of a battery state of the device. In some implementations, the indicator 128 may be green when the battery is sufficiently charged, yellow as battery level begins to deplete in the device, and red when the battery is beyond its usable life. Similar or other indications may also be provided via the visual indicator 128 using other visual cues. For example, the visual indicator 128 may blink to convey information.

The toothbrush 100 may be constructed of a number of known materials or combinations of materials having suitable rigidity for conventional toothbrush use. For example, materials may be chosen for their rigidity for grasping and/or handling of the toothbrush and supporting the tooth cleaning elements 112. Suitable exemplary materials may be used in a toothbrush include, but are not limited to, hard plastics, such as polyethylene, polypropylene cone, polyimide, polyester, cellulosic, SAN, acrylic, ABS, and other thermoplastics suitable for toothbrush manufacture. The various portions and features the toothbrush 100 may be made of the same or different materials in various embodiments.

Figure 2:
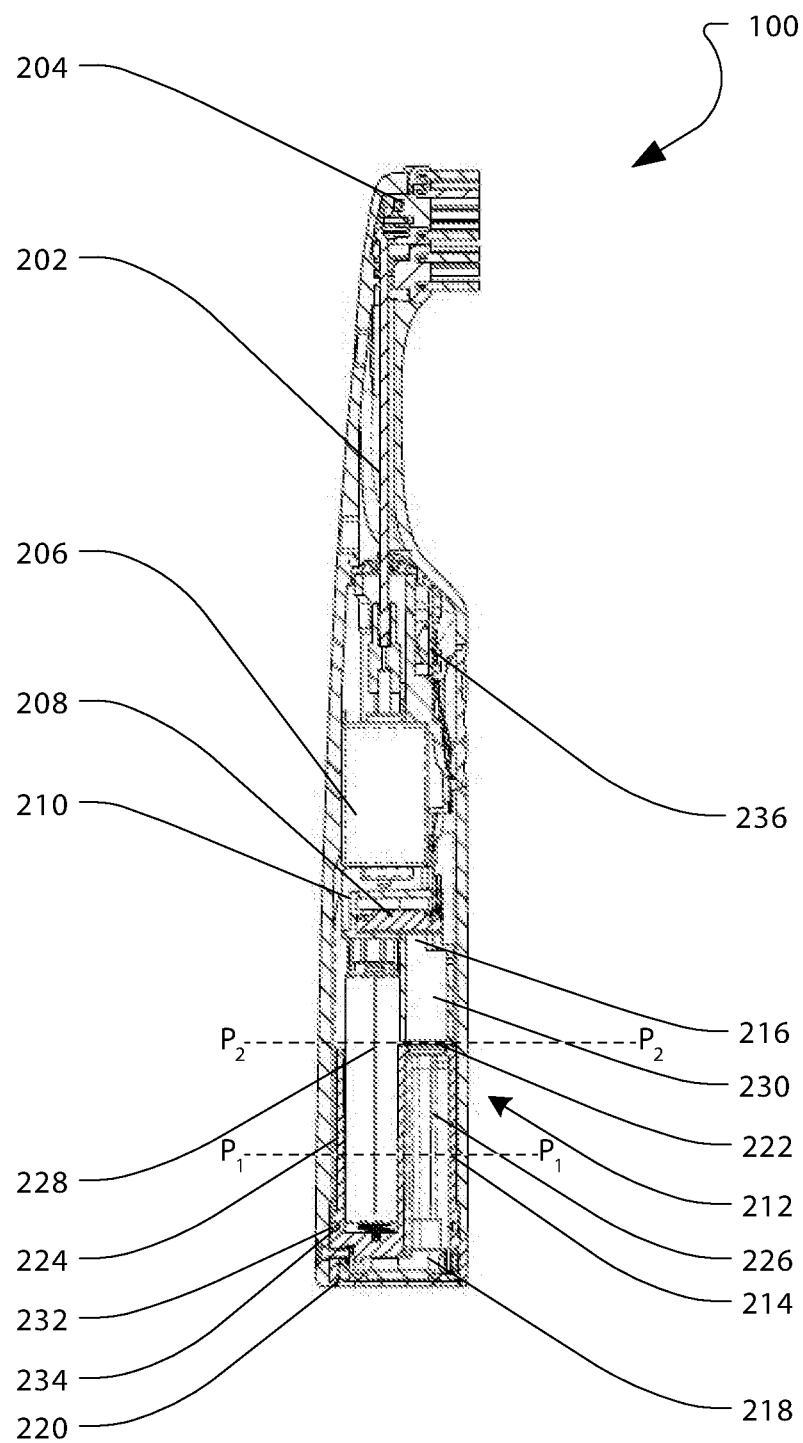
FIG. 2 is a section view of the oral care device illustrated in FIGS. 1A and 1B, taken along section line 2-2 in FIG. 1A.

FIG. 2 is a cross-sectional view taken along section line 2-2 in FIG. 1A. As illustrated in FIG. 2, the body 102 including the handle 106 and the neck 108, as well as the head 110 are hollow, defining a plurality of cavities adapted to contain additional elements of the powered toothbrush 100. For example, an oscillator arm 202 is disposed in the neck and attaches at a distal end to an oscillating plate 204 on which a plurality of the tooth cleaning elements 112 are disposed. An opposite, proximal end of the oscillator arm 202 is coupled to an output arm of a motor 206, disposed in the body 102. Driving the motor 206 oscillates the oscillator arm 202, which in turn oscillates the oscillating plate 204. The result is movement of the tooth cleaning elements 112. As illustrated, the motor 206 may be powered by a power source, such as a battery 228 disposed in the handle 106.

A speaker 208 also is disposed in the body 102, spaced from the proximal end 104 of the body 102. In the illustration, the speaker 208 is mounted to a support 210, and the support 210 is fixed relative to a sidewall of the handle 106. The speaker is arranged to project sound waves generally along the axial direction, toward the proximal end 104.

An audio chamber 212 is provided between the speaker 208 and the proximal end 104 of the body 102. The audio chamber 212 generally is an elongate opening that directs sounds waves emitted from the speaker 208. In the configuration of FIG. 2, the speaker is disposed to emit sound in a direction generally along a longitudinal axis of the toothbrush 100, toward the proximal end 104. The audio chamber 212 is bounded by one or more sidewalls 214 extending between a first opening 216 proximate the speaker 208 and a second opening 218 proximate the proximal end 104 of the body 102. The first and second openings 216, 218 are spaced along the longitudinal axis of the toothbrush 100. In other embodiments, the audio chamber may be tipped, tilted, rotated, or otherwise configured. Moreover, interior surfaces of the sidewall 214 may be tapered or otherwise contoured such that the audio chamber 212 has relatively narrower and wider segments along the longitudinal direction. For example, in some implementations and without limitation, the audio chamber may be relatively narrower proximate the first opening 216 and relatively wider proximate the second opening 218, e.g., such that the chamber 212 is substantially frusto-conical. In preferred embodiments, however, the audio chamber 212 is arranged to direct sound waves emitted from the speaker 208 toward the proximal end 104.

Also illustrated more clearly in FIG. 2, the lateral openings 118 are formed through the sidewall of the base 114 near the proximal end 104. The openings 118 extend from an outer surface of the base 114 into the audio chamber 212. Accordingly, the openings 118 provide a passageway from inside the audio chamber to outside the toothbrush 100. Other openings may provide a similar passageway. For example, axial openings could extend from an exterior surface of an end cap 220 covering the second opening 218 of the audio chamber 212 into the audio chamber. In this arrangement, sound emitted from the speaker 208 is directed into the audio chamber 212 and out the lateral openings 118 and any other openings disposed at the proximal end 104. The audio chamber 212 may act as a mechanical amplifier, e.g., a resonance chamber, to amplify the sound emitted from the speaker. In other embodiments, the lateral openings 118 and/or other openings may not be provided, and the sound may exit the body 102 through the second opening 218, e.g., out the bottom of the handle. In such an embodiment, the base 114 may not include the end cap 220, or the end cap 220 may include a larger, axial aperture, e.g., the same size as or bigger than the second opening 218.

In addition to amplifying the sound, the audio chamber 212 also allows placement of the sound outlet at a location spaced from the speaker. This may beneficially allow sound to exit the toothbrush at locations less likely to be covered or muffled during brushing. For example, it is unlikely that a user would hold the toothbrush 100 during use in a manner that covers the lateral openings 118 or other openings proximate the distal end. In alternative embodiments, the audio chamber 212 could be shorter, or the holes could be provided nearer the user interface 122. In that location, however, a user may be more likely to grip the toothbrush in a manner that covers the speaker 208.

The audio chamber 212 also may protect the speaker and/or other electronics also allows for placement of the speaker 208 farther from any opening through which water, toothpaste, or other elements that may have a negative effect on the speaker may enter the toothbrush. In some embodiments, the lateral openings 118 and/or any other openings may be through holes, and water or other foreign substances may enter the audio channel 212 via those openings. However, the length of the audio chamber 212 will provide some deterrent to foreign substances reaching the speaker.

Although not required, in some embodiments, a physical barrier may also be provided in the audio chamber, e.g., to prevent contamination. For instance, FIG. 2 illustrates a membrane 222 provided in the audio chamber 212. The membrane 222 extends across the opening of the audio chamber 212, e.g., to occlude the audio chamber 212. The membrane 222 preferably allows sound to pass, but inhibits contaminants such as water, toothpaste, and the like from traversing the audio chamber 212 and contacting the speaker or other elements disposed in the toothbrush 100. In some implementations, the membrane 222 may be formed of a liquid-impermeable, but sound-permeable material. The membrane 222 may also be vapor or gas-permeable, e.g., to allow off gasses, such as hydrogen, from the electronic components to exhaust to the atmosphere. For example, the membrane 222 may comprise polytetrafluoroethylene, although other materials, including but not limited to micro-perforated materials or woven materials may also be used. In still other embodiments, the membrane 222 may be a more rigid material, with holes formed therethrough. For example, holes may be axially formed through the membrane 222.

The membrane 222 may be disposed at any position between the first opening 216 and the second opening 218 of the audio chamber. The membrane 222 may lie in a second transverse plane ($P_2$) which is transverse to the longitudinal axis of the toothbrush 100. Moreover, more than one membrane may be provided. The membrane 222 may be attached to the audio chamber using any number of conventional methods. For example, but without limitation, the membrane 222 may be fixed by adhesion, welding, e.g., ultrasonic welding, or mechanical means. As noted above, the membrane 222 is optional, and may not be provided in some implementations.

As noted above, the base 114 may be separable from the handle 106. In the illustrations, the base 114 is formed as a cartridge that is selectively receivable in a receptacle formed in the proximal end of the handle 106. The base 114 generally includes the end cap 220 formed as a substantially planar cap, a battery compartment 224, and a proximal portion 226 of the audio chamber 212. The base 114 may be completely separable from the handle 106, or it may be slidable, pivotable, or otherwise movable relative to the handle. The base and the handle may also have complementary features that prevent complete removal of the base 114 from the handle 106. Such features may include a catch, a stop, of the like. An arrangement that is not completely separable may be desirable when elements connect to features on both the base 114 and in the body 102. For example, electrical leads may contact the battery in the base 114 and extend to the speaker 208 in the handle 106.

The battery compartment 224 is sized to receive one or more batteries 228 for powering the toothbrush 100. The battery compartment 224 and the audio chamber 212 are located such that a first transverse plane ($P_1$) transverse to the longitudinal axis of the toothbrush 100 intersects both the battery compartment 224 and the audio chamber 212. Battery contacts may also be provided in the battery compartment 224. The batteries 228 may be any conventional power source, including but not limited to dry cell batteries, rechargeable batteries, or the like.

The proximal portion 226 of the audio chamber 212 is aligned with a distal portion 230 of the audio chamber 212 to form the complete audio chamber 212 when the base 114 is disposed in the handle 106. In alternative embodiments, the proximal portion 226 and the distal portion 230 of the audio chamber 212 may be relatively longer and/or shorter. The membrane 222, when present, may be disposed over an open end of the proximal portion 226 or over an open end of the distal portion 230 of the audio chamber 212. Alternatively, the membrane 222 may be disposed at any distance spaced along either the proximal portion 226 or the distal portion 230. When the membrane 222 is disposed to cover one of the proximate portion 226 or the distal portion 230, the membrane 222 may also act as a seal between the proximal portion 226 and the distal portion 230. For example, an open edge of the proximal portion 226 or the distal portion 230 that does not include the membrane 222 may contact the membrane when the base 114 is received in the handle 106. Additionally or alternatively, a seal, such as an O-ring or the like, including a foam O-ring, may be arranged between the proximate portion 226 and the distal portion 230 to prevent flow of contaminants and/or sound loss at the junction of the two portions 226, 230.

Additional seals also may be provided between the base 114 and the handle 106. For example, a seal 232, which may be an O-ring, may be retained in a circumferential slot 234 formed around the base 114. In alternative embodiments, the seal may be a sliding seal, a gasket, or any other seal between the base 114 and an internal surface of the body 102.

The toothbrush 100 may include additional features. For example, a controller 236 may also be included, and may be in communication with the user interface 122. The controller 236 may be a printed circuit board or other electronics and may perform myriad functions. For example, the controller may include timing circuitry or programming that turns off the motor 206 after a certain amount of time. The controller may also or alternatively include one or more routines or programs that drive the motor, e.g., to move the tooth cleaning elements in a predetermined manner. The controller 236 may also include an audio source, which may include one or more audio files or recordings. The user may be able to choose an audio file in some embodiments from among audio stored in memory associated with the controller.

The toothbrush illustrated in FIGS. 1A, 1B, and 2 may be manufactured as a number of pieces and then assembled. As noted above, the base may be separable from the body 102. In addition, a chassis or other mounting structure may carry or support several features of the toothbrush, including but not limited to the motor 206, the controller 236, switches operable via the user interface 122, the speaker 208, and/or the audio chamber 212. For example, the support 210 may be part of a larger chassis that is pre-assembled for subsequent placement in the toothbrush 100 cavity. Forming the electronic and control elements as a separate assembly may allow for easier manufacturing, assembly, and/or testing.

Modifications to the toothbrush 100 also are anticipated, and the disclosure is not limited to the embodiments in the Figures. For example, although the speaker is illustrated as being fixed in the body 102, such is not required. The speaker may be mounted on the base 104. As required, electrical contacts or the like may be provided to promote electrical connection of the speaker to the controller.

In other implementations, the base 114 may include fewer components. For example, the base may include only one, or neither, of the battery compartment or the proximal portion of the 226 of the audio chamber. In some embodiments, the base 114 may only include the end cap 220. Removal of the base 114 may allow a user to insert batteries into the handle 106, for example. Moreover, the entirety of the audio chamber may be fixed in the body 102.

Although example embodiments have been described in language specific to the structural features and/or methodological acts, the claims are not necessarily limited to the specific features or acts described. Rather, the specific features and acts are disclosed as illustrative forms of implementing the example embodiments.

What is claimed is:

1. An oral care implement comprising:
   an elongate body extending from a proximal end to a distal end along a longitudinal axis;
   a head disposed at the distal end of the elongate body;
   a tooth cleaning element disposed at the head;
   a speaker disposed in the elongate body at a distance spaced from the proximal end of the elongate body to emit sound toward the proximal end of the elongate body;
   a sound chamber comprising an elongate internal space extending from a first opening proximate the speaker to a second opening proximate the proximal end of the elongate body, wherein sound emitted from the speaker passes through the sound chamber and the sound chamber extends along the longitudinal axis;
   a water-impermeable membrane occluding the sound chamber between the speaker and the proximal end, wherein sound waves pass through the water-impermeable membrane; and
   a battery compartment extending along the longitudinal axis, a first transverse plane transverse to the longitudinal axis and intersecting both the battery compartment and the elongate internal space of the sound chamber.

2. The oral care implement of claim 1, wherein the water-impermeable membrane lies in a second transverse plane transverse to the longitudinal axis, the second transverse plane located between the speaker and the proximal end.

3. The oral care implement of claim 1, further comprising one or more lateral openings extending from an external surface of the elongate body to an internal surface of the sound chamber.

4. The oral care implement of claim 3, wherein the one or more lateral openings are adjacent the proximal end of the elongate body.

5. The oral care implement of claim 1, further comprising an end cap disposed to cover the second opening.

6. The oral care implement of claim 1, further comprising one or more axial openings extending from an external surface of the proximal end of the elongate body to an internal surface of the sound chamber.

7. The oral care implement of claim 1, further comprising a power source disposed in the elongate body.

8. The oral care implement of claim 1, wherein the sound chamber comprises a first portion and a second portion aligned with the first portion, and further comprising a removable cartridge disposed in the elongate body, wherein a first portion of the sound chamber is disposed in the elongate body and the removable cartridge comprises the second portion of the sound chamber.

9. The oral care implement of claim 8, further comprising a seal sealing the removable cartridge relative to the elongate body.

10. The oral care implement of claim 8, further comprising a seal sealing the first portion of the sound chamber relative to the second portion of the sound chamber.

11. The oral care implement of claim 8, wherein the removable cartridge comprises a battery compartment.

12. The oral care implement of claim 8, further comprising one or more openings extending from an external surface of the cartridge to an internal surface of the second portion of the sound chamber.

13. The oral care implement of claim 2, wherein the water-impermeable membrane comprises polytetrafluoroethylene.

14. An oral care implement comprising:
a handle defining a receptacle accessible via a proximal end of the handle, the handle having a longitudinal axis;
a speaker disposed in the handle at a distance from the proximal end and positioned to transmit sound toward the proximal end;
a first sound chamber extending from a position proximate the speaker to the receptacle; and
a cartridge disposed in the receptacle, the cartridge comprising a second sound chamber aligned with the first sound chamber;
wherein the first and second sound chambers are axially between the speaker and the proximal end along the longitudinal axis of the handle.

15. The oral care implement of claim 14, further comprising a seal disposed between the cartridge and the receptacle.

16. The oral care implement of claim 15, wherein the seal is disposed between the first sound chamber and the second sound chamber.

17. The oral care implement of claim 14, further comprising a water impermeable membrane extending laterally across the first sound chamber or the second sound chamber.

18. The oral care implement of claim 14, further comprising one or more openings extending from an exterior surface of the cartridge to the second sound chamber.

19. The oral care implement of claim 18, wherein the one or more openings are adjacent the proximal end of the handle.

20. The oral care implement of claim 18, wherein the one or more openings are disposed outside the receptacle.

21. The oral care implement of claim 18, wherein the one or more openings are spaced from the proximal end of the handle by a distance along an axial dimension.

22. The oral care implement of claim 14, wherein the cartridge contains a power source.

23. The oral care implement of claim 22, wherein the power source comprises a battery.

24. An oral care implement comprising:
a handle having an axis and a cavity, the cavity extending along the axis and open at a proximal end of the handle;
a speaker fixedly disposed in the cavity of the handle and positioned to transmit sound toward the proximal end;
a first sound chamber extending from the speaker toward the proximal end of the handle along the axis; and
a removable cartridge disposed in the cavity, the cartridge comprising a second sound chamber aligned with the first sound chamber and extending from the first sound chamber to the proximal end along the axis.

* * * * *